Figure 1:
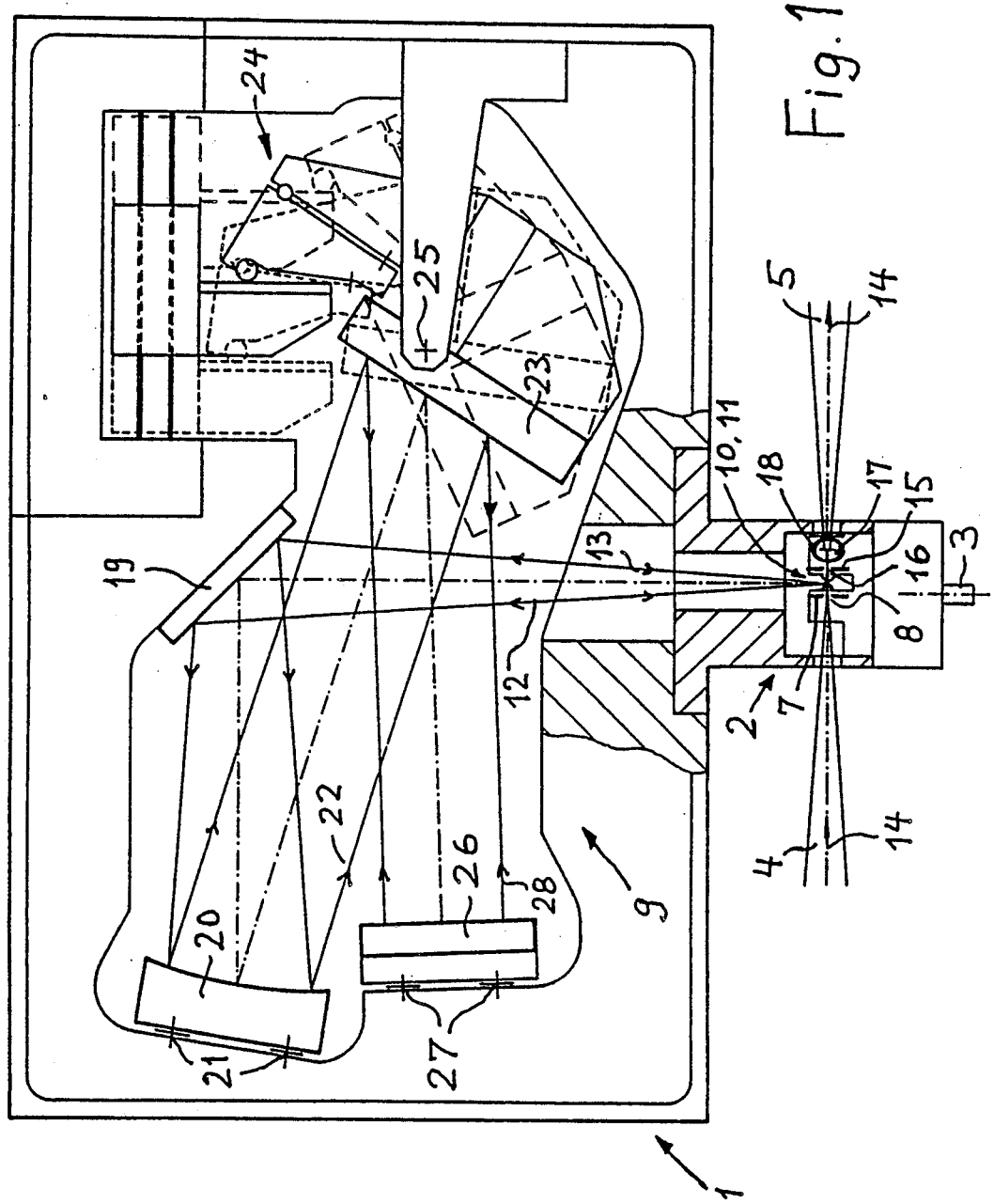

United States Patent [19]
Riedel et al.

[11] Patent Number: 4,995,725
[45] Date of Patent: Feb. 26, 1991

[54] MONOCHROMATOR ARRANGEMENT

[75] Inventors: Wolfgang Riedel, Neuenburg; Manfred Knothe; Roland Grisar, both of Freiburg; Helmut Wolf, Merzhausen, all of Fed. Rep. of Germany; Horst M. Preier, Acton, Mass.

[73] Assignee: Fraunhofer-Gesellschaft zur Forderung der Angewandten Forshung E.V., Munich, Fed. Rep. of Germany

[21] Appl. No.: 237,735
[22] PCT Filed: Nov. 19, 1987
[86] PCT No.: PCT/DE87/00528
 § 371 Date: Jul. 21, 1988
 § 102(e) Date: Jul. 21, 1988
[87] PCT Pub. No.: WO88/04036
 PCT Pub. Date: Jun. 2, 1988

[30] Foreign Application Priority Data
Nov. 24, 1986 [DE] Fed. Rep. of Germany ....... 3640044

[51] Int. Cl.⁵ .............................................. G01J 3/18
[52] U.S. Cl. .................................................. 356/334
[58] Field of Search ............. 356/331, 332, 333, 334, 356/305

[56] References Cited
U.S. PATENT DOCUMENTS

| | | | |
|---|---|---|---|
| 3,069,967 | 12/1962 | White et al. | 356/334 |
| 3,700,898 | 10/1972 | Macleod | 250/343 |
| 3,749,498 | 7/1973 | Shimomura | 356/333 |
| 3,753,618 | 8/1973 | Haley | 356/334 |

FOREIGN PATENT DOCUMENTS

| | | | |
|---|---|---|---|
| 3400299 | 7/1984 | Fed. Rep. of Germany | |
| 136928 | 5/1960 | U.S.S.R. | 356/332 |

OTHER PUBLICATIONS

Fresenius Zeitsthrift publication "Gas Analysis with IR-Diode Laser Spectrometers", 1984, pp. 347-349.

Primary Examiner—F. L. Evans
Attorney, Agent, or Firm—Jeffers, Hoffman & Niewyk

[57] ABSTRACT

A monochromator apparatus comprises a monochromator (9) and a reversing device (2) which, with the aid of four reversing mirrors (10, 11, 17, 18) shifts the exit ray (13), of a monochromator (9) introduced in an intermediate focus of an external path of rays (4, 5), in the external path of rays (5) so that the external path of rays (4, 5) will not be influenced by the presence or absence of the monochromator apparatus (2, 9).

19 Claims, 3 Drawing Sheets

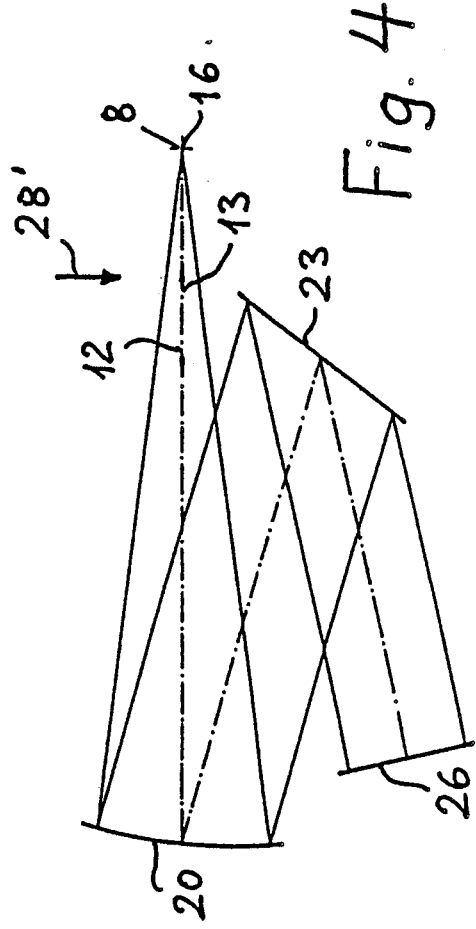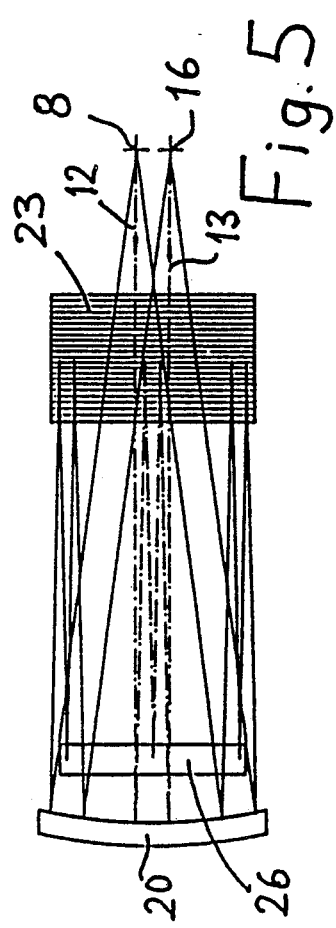

MONOCHROMATOR ARRANGEMENT

The invention concerns a monochromator arrangement with an adjustable grid monochromator whose path of rays features an entrance focus and an exit focus which relative to the entrance focus is offset sideways.

Known from the German patent application No. 34 00 299 C 2 and Fresenius Z Anal. Chemi (1984) 317:347–349, such monochromator arrangements are employed in the use of adjustable infrared diode lasers for high-resolution spectroscopy, for instance in the quantitative gas analysts, in order to separate the spectrum emitted by the diode laser in individual laser modes respectively laser frequencies while blanking out the remaining modes. High-resolution grid monochromators are used for mode selection.

In prior monochromator arrangements it is for adjustment purposes necessary to move a plane mirror within the monochromator arrangement before the diffraction grid. Since such a mirror is of necessity arranged before the diffraction grid, the illumination of the following lenses will change when the mirror is moved in. An optimization of the lighting is thus not achievable for all cases.

Basing on this prior art, the problem underlying the invention is to provide a monochromator arrangement which retroactively can be inserted in an external path of rays of a spectrometer that features an intermediate focus, after the spectrometer has already been adjusted, where this adjustment is fully retained.

This problem is inventionally solved in that with the grid monochromator there is coordinated a reversing device that features a flat reversing mirror through which the entrance focus and the exit focus are reproduced in one and the same intermediate focus of an external path of rays that extends transverse to the connecting line between the entrance focus and the exit focus of the grid monochromator.

In the inventional monochromator arrangement, adjustment and operation of the entire spectrometer arrangement are possible without monochromator.

In the inventional monochromator arrangement, the entrance and exit ray are so reversed by the reversing mirror that the entrance focus and the exit focus will coincide, with the entrance and exit directions being identical. In this way it is possible to operate the monochromator arrangement in transparency in an intermediate focus of an optical laser spectrometer setup, without influencing the external path of rays.

In accordance with the instant invention, the diffraction grid is utilized twice, and under a large angle in the monochromator arrangement, for increasing the dispersion. Accomplished thereby is a sufficiently high resolution for mode selection also with a small grid of only about 30 mm edge length. Owing to the possibility of requiring only a small grid, the monochromator arrangement can be built very small, enabling a closely spaced serial arrangement. An extra-axial parabolic mirror is used in the monochromator as a collimator in order to obtain a reproduction that is limited in diffraction and free of astigmatism.

Owing to the reversing device of the monochromator arrangement it is possible to move the entrance focus of the monochromator at the place of an intermediate focus of the external path of rays and to reproduce the exit focus of the monochromator, by reflection, as well in the same intermediate focus in such a way that the monochromator will restore the external path of rays and appears from outside the same as an aperture with a spectral filter effect. The reversing device is an integral part of the monochromator arrangement. By means of a centering pin it is possible to introduce the monochromator arrangement in reproducibly accurate fashion in a free intermediate focus of the external spectrometer arrangement.

Suitable developments and designs of the invention are characterized in the subclaims.

The invention will be more fully described hereafter with the aid of an embodiment illustrated in the drawing.

Figure 2:
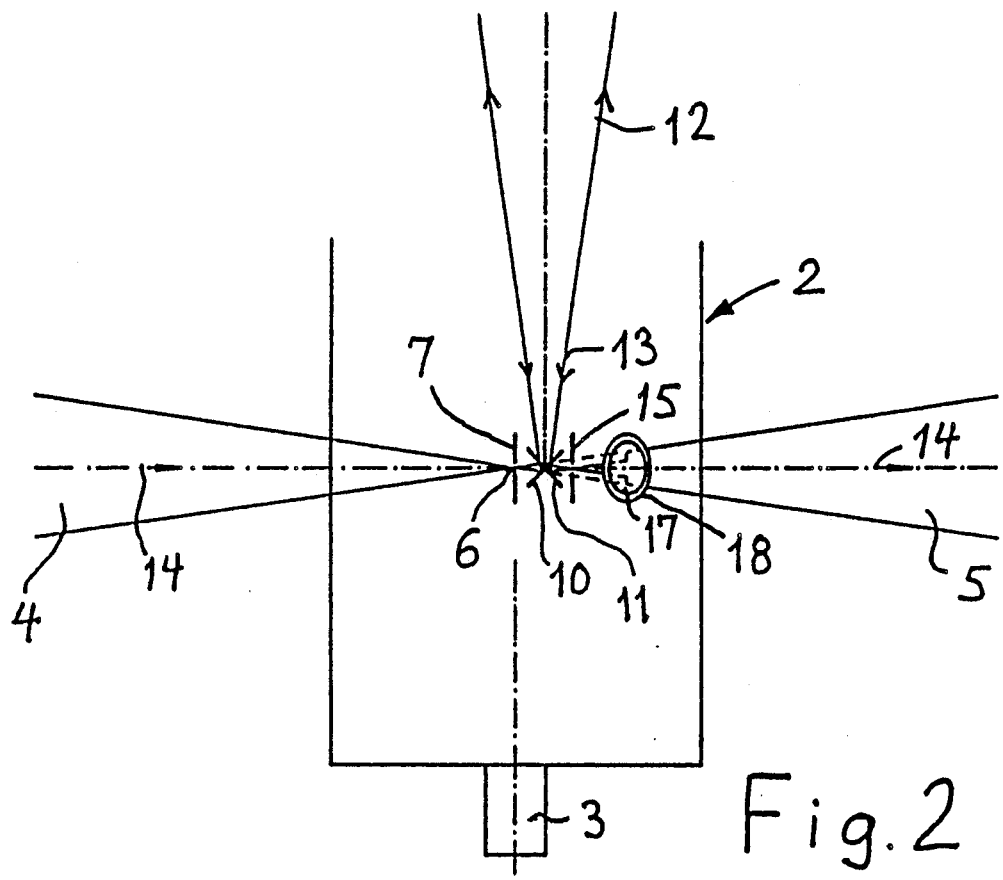
Figure 3:
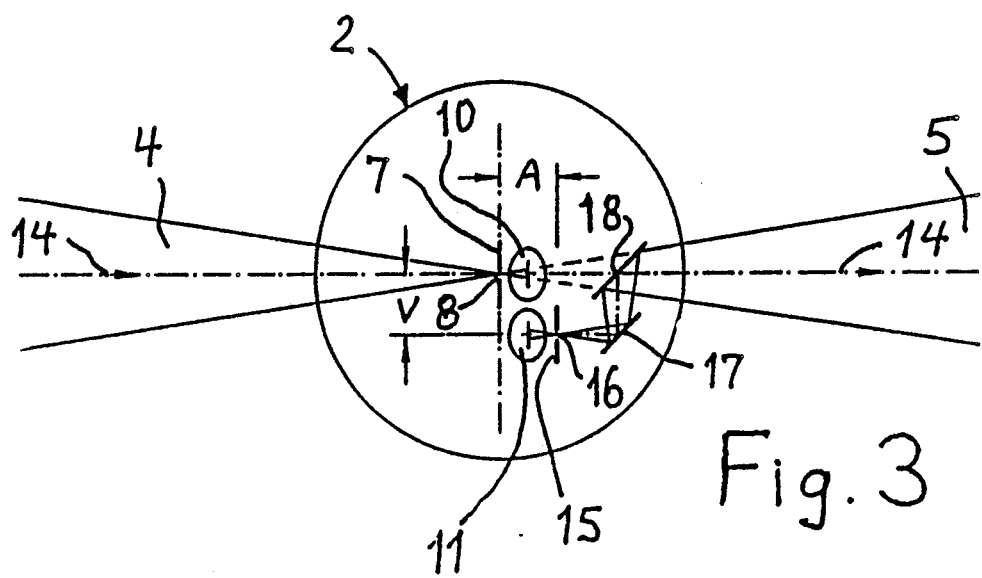

FIG. 1 shows a monochromator arrangement according to the invention in a lateral view, partly in section;

FIG. 2, the reversing device of the monochromator arrangement, in a scaled-up side view;

FIG. 3, the reversing device according to FIG. 2 in a view from above;

FIG. 4, the basic path of rays of the monochromator as a schematic side view; and FIG. 5, the basic path of rays of the monochromator coordinated with the reversing device, in plan view.

The monochromator arrangement illustrated in FIG. 1 comprises a monochromator housing 1 and a reversing device housing 2 which is designed as a plug-in part and provided, on its bottom end in FIG. 1, with a centering pin 3.

To the left and right of the reversing device housing 2, a converging and entering external path of rays 4 and a diverging exiting external path of rays 5 can be seen. The converging external path of rays 4 originates from the light of an adjustable infrared laser, which is not illustrated in the drawing and is used in high resolution spectroscopy, for instance in the quantitative gas analysis. The light of the laser not illustrated in the drawing is focused on an intermediate focus 6 which is coordinated with the converging external path of rays 4 and the diverging external path of rays 5. The latter proceeds to a measuring section not illustrated in the drawing and finally to a detector not illustrated in the drawing.

The intermediate focus 6 is located within the reversing device housing 2, as can be seen best from FIGS. 2 and 3, in the opening of the entrance aperture 7 of the monochromator arrangement. The opening of the entrance aperture 7 likewise forms the entrance focus 8 for the monochromator 9 arranged in the monochromator housing 1. The longitudinal axis of the centering pin 3 extends through the intermediate focus 6 and the entrance focus 8.

When the monochromator arrangement illustrated in FIG. 1 is removed from the path of rays of the not illustrated laser spectrometer, such will not change the converging external path of rays 4 illustrated in FIG. 1, bottom, and the diverging external path of rays 5 in its position. The monochromator arrangement illustrated in FIG. 1 acts therefore the same as an aperture with spectral filter effect.

Once the light of the converging external path of rays 4 has passed the entrance aperture 7 in the reversing device housing 2, the light in the diverging external path of rays 5 leaving the entrance aperture 7 proceeds in the direction of propagation of the light, shortly behind the entrance aperture 7, onto a first reversing mirror 10 which, in FIG. 1, together with a second reversing mirror 11 has in side view the shape of the letter X and can be seen more clearly in FIGS. 2 and 3.

The first reversing mirror 10 deflects the laser light, in FIGS. 1 and 2, by 90° upward, the deflected ray being marked 12 in FIGS. 1 and 2. The deflected ray 12 forms the entrance ray for the monochromator 9 arranged in the monochromator housing 1. The exit ray 13 of the monochromator 9 is illustrated in FIGS. 1, 2 and 4 in a fashion overlapping the entrance ray 12 although, as can be seen best from FIGS. 3 and 5, the exit ray 13 is offset transverse to the direction of propagation of the external path of rays 4, 5, relative to the entrance ray 12, as it leaves the monochromator 9, so that the exit ray 13 impinges on the second reversing mirror 11 which, as illustrated in FIG. 3, is offset sideways and transverse to the direction of propagation 14 of the external path of rays 4, 5 by an amount V.

Corresponding to the lateral offset of the second reversing mirror 11, an exit aperture 15 is provided in the housing 2 of the reversing device, offset relative to the entrance aperture 7. As can be seen from FIG. 3, the exit aperture 15 is offset relative to the entrance aperture 7, transverse to the direction of propagation 14, by the same amount V as the second reversing mirror 11. Besides, the exit aperture 15 is shifted by the amount A in the direction of propagation 14, the amount A equaling the offset V.

The exit focus 16 of the monochromator 9, in properly adjusted condition, is located exactly in the opening of the exit aperture 15.

As can be seen best from FIG. 3, the second reversing mirror 11, which relative to the first reversing mirror 10 is tilted by 90°, deflects the exit ray 13 of the monochromator 9 to a third reversing mirror 17 which reflects the exit ray 13 of the monochromator 9 opposite to the direction of the offset of the second reversing mirror 11 relative to the first reversing mirror 10.

A fourth reversing mirror 18 is arranged in the reversing device housing 2 in the extension of the diverging beam impinging on the first reversing mirror 10 and coinciding in its position with the diverging external path of rays 5, said mirror deflecting the beam leaving the third reversing mirror 17 by 90° in the direction of propagation 14, so that the beam leaving the fourth reversing mirror 18 has the same position as the diverging external path of rays 5. The mirror arrangement in the reversing device housing 2 thus causes, for one, that the entrance focus of the monochromator 9 is being moved to the location of the intermediate focus 6 of the external path of rays 4, 5 and, for another, that the exit focus 16 of the monochromator 9 is being reproduced by mirror reflection on the reversing mirrors 11, 17 and 18 as well as on the same intermediate focus 6, so that the monochromator arrangement leaves the external path of rays 4, 5 unchanged.

Following the description of the reversing device contained in the reversing device housing 2, the structure of the monochromator 9 in the housing 1 shall be discussed now. To that end, reference is made, in addition to FIG. 1, to FIGS. 4 and 5.

The entrance ray 12 of the monochromator 9 proceeds first to a folding mirror 19 which in the monochromator housing 1 is inclined by 45° relative to the longitudinal axis of the centering pin 3. Subsequent to the reflection on the folding mirror 19, the ray proceeds to an extra-axial parabolic mirror which is provided as a collimator mirror and mounted in the housing 1 with the aid of an adjustable three-point support 21. The parabolic mirror 20 collimates the rays to a parallel ray 22 that proceeds then to the grid 23. From the grid 23, which by a sine drive 24 can be tilted about an axis 25 perpendicular to the direction of propagation in the external path of rays 4, 5, the ray is diffracted toward a plane mirror 26 which with the aid of an adjustable threepoint support 27 is mounted inside the housing 1. The plane of dispersion of the grid 23 extends parallel with the drawing plane extending between the entrance focus 8 and the exit focus 16. In the adjustment illustrated in FIG. 1, the incidence on the plane mirror 26 is essentially below the drawing plane, which mirror reflects the incident rays obliquely in the direction above the drawing plane. Subsequent to the reflection on the plane mirror 26, the ray 28 is diffracted a second time on the grid 23 and then focused by the parabolic mirror 20 in the exit focus 16, which in FIG. 4 is located above the drawing plane, whereas the entrance plane 8 is located below the drawing plane in FIG. 4.

For clarification of the position of the entrance focus 8 and exit focus 16, FIG. 5 shows an illustration that derives from FIG. 4 viewed in the direction of an arrow 28'.

With a proper grid position, the ray is diffracted toward the parabolic mirror 20 already in the first diffraction on the grid 23. But the parabolic mirror 20 is so adjusted that the incidence of the focused ray can then not be in the regular exit focus 16, thus avoiding an erroneous measurement of the laser wave-length. In a regular passage, the ray is focused toward the exit focus 16 by alignment of the plane mirror 26.

As will be evident to the expert from the above description, the entrance ray 12 and the exit ray 13 are offset only transverse to the plane of dispersion of the grid 23.

We claim:

1. A monochromator apparatus comprising:
   a monochromator;
   an entrance aperture defining an entrance focus for said apparatus, said entrance aperture located on a first axis which defines the direction of propagation of light rays entering said entrance aperture, said entering light rays defining a first intermediate focus;
   an exit aperture defining an exit focus for said apparatus, said exit aperture defining a second axis which is abaxially offset from said first axis by a lateral distance;
   a diffraction grid; and
   a plurality of reversing mirrors for intercepting light rays which pass through said entrance aperture and for reflecting said rays onto said grid from said through said exit aperture and from the exit aperture to the exit of said monochromator apparatus, said light rays exiting said monochromator apparatus defining a second intermediate focus at the location of said first intermediate focus.

2. Monochromator apparatus according to claim 1, characterized in that said monochromator includes an extra-axial parabolic mirror for collimating light rays entering through said entrance focus and for reflecting said light rays to said grid for diffracting said light rays toward a plane mirror which reflects the received light rays back to said grid where said light rays are diffracted a second time before said rays are focused by said parabolic mirror on said exit focus.

3. Monochromator apparatus according to claim 1, including a reversing device characterized in that the reversing device changes the direction of said entering light rays by means of a first of said plurality of reversing mirrors to a direction oriented perpendicularly to the direction of said first axis.

4. Monochromator apparatus according to claim 3, wherein a second of said plurality of reversing mirrors reflects said light rays received from said grid along said second axis.

5. Monochromator apparatus according to claim 4, characterized in that said entrance and exit apertures are arranged to respectively direct said light rays to and from said first and second reversing mirrors.

6. Monochromator apparatus according to claim 5, characterized in that the entrance aperture is located at said first intermediate focus.

7. Monochromator apparatus according to claim 4, wherein third and fourth reversing mirrors of said plurality of reversing mirrors change the direction of light rays reflected by the second reversing mirror into a direction coaxial with said first axis.

8. Monochromator apparatus according to claim 5, wherein said entrance and exit apertures rae separated by a longitudinal distance in the direction of said first axis and wherein said lateral offset distance of said apertures equals said longitudinal distance.

9. Monochromator apparatus according to claim 4, characterized in that said first and second reversing mirrors are arranged with their respective axes at 90° relative to each other.

10. Monochromator apparatus according to claim 7, wherein the distance between said third and fourth reversing mirrors equals said lateral offset distance, and wherein the sum of the distance between the exit aperture and the third reversing mirror and the distance between the third reversing mirror and the fourth reversing mirror equals the distance between the entrance aperture and the fourth reversing mirror.

11. Monochromator apparatus according to claim 1, wherein the monochromator includes an extra-axial parabolic mirror for collimating light rays entering through said entrance focus and for reflecting said light rays to said grid for diffracting said light rays toward a plane mirror which reflects the received light rays back to said grid where said light rays are diffracted a second time before said light rays are focused by said parabolic mirror on said exit focus and wherein the apparatus includes a reversing device which changes the direction of said entering light rays by means of a first of said plurality of reversing mirrors to a direction oriented perpendicularly to the direction of said first axis.

12. Monochromator apparatus according to claim 5, wherein said entrance and exit apertures are arranged to respectively direct said light rays to and from said first and second reversing mirrors, and wherein third and fourth reversing mirrors of said plurality of reversing mirrors change the direction of light rays reflected by said second reversing mirror into a direction coaxial with said first axis.

13. Monochromator apparatus according to claim 5, characterized in that said entrance aperture is located at said intermediate focus, and wherein third and fourth reversing mirrors of said plurality of reversing mirrors change the direction of light rays reflected by said second reversing mirror into a direction coaxial with said first axis.

14. Monochromator apparatus according to claim 5, wherein said entrance aperture is located at said first intermediate focus and wherein said entrance and exit apertures are separated by a longitudinal distance in the direction of said first axis and wherein said lateral offset distance of said apertures equals said longitudinal distance.

15. Monochromator apparatus according to claim 5, wherein said entrance and exit apertures are arranged to respectively direct said light rays to and from said first and second reversing mirrors, and wherein first and second reversing mirrors are arranged with their respective axes at 90° relative to each other.

16. Monochromator apparatus according to claim 5, characterized in that said entrance aperture is located at said first intermediate focus, and wherein said first and second reversing mirrors are arranged with their respective axes at 90° relative to each other.

17. Monochromator apparatus according to claim 4, wherein third and fourth reversing mirrors of said plurality of reversing mirrors change the direction of light rays reflected by said second reversing mirror into a direction coaxial with said first axis, and wherein said first and second reversing mirrors are arranged with their respective axes at 90° relative to each other.

18. Monochromator apparatus according to claim 5, wherein said entrance and exit apertures are separated by a longitudinal distance in the direction of said first axis, wherein said lateral offset distance of said apertures equals said longitudinal distance and wherein said first and second reversing mirrors are arranged with their respective axes at 90° relative to each other.

19. Monochromator apparatus according to claim 4, wherein third and fourth reversing mirrors of said plurality of mirrors reverse the direction of light rays reflected by said second reversing mirror, wherein the distance between said third and fourth reversing mirrors equals said lateral offset distance, and wherein the sum of the distance between the exit aperture and the third reversing mirror and the distance between the third reversing mirror and the fourth reversing mirror equals the distance between the entrance aperture and the fourth reversing mirror.

* * * * *